(12) United States Patent
Wang

(10) Patent No.: US 8,582,101 B2
(45) Date of Patent: Nov. 12, 2013

(54) HIGH THROUGHPUT BIREFRINGENCE MEASUREMENT

(75) Inventor: Baoliang Wang, Hillsboro, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 216 days.

(21) Appl. No.: 13/002,650

(22) PCT Filed: Jul. 2, 2009

(86) PCT No.: PCT/US2009/049614
§ 371 (c)(1),
(2), (4) Date: Mar. 26, 2011

(87) PCT Pub. No.: WO2010/005874
PCT Pub. Date: Jan. 14, 2010

(65) Prior Publication Data
US 2011/0181883 A1    Jul. 28, 2011

Related U.S. Application Data

(60) Provisional application No. 61/079,120, filed on Jul. 8, 2008.

(51) Int. Cl.
*G01J 4/00* (2006.01)

(52) U.S. Cl.
USPC .......................................... 356/370; 356/364

(58) Field of Classification Search
USPC .......... 356/364–370, 450, 453, 491; 250/225, 250/227.17, 252.1, 227.14, 216, 200
See application file for complete search history.

(56) References Cited

U.S. PATENT DOCUMENTS

| 3,566,130 | A | * | 2/1971 | Aldrich et al. .......... 250/214 LA |
| 6,473,179 | B1 | * | 10/2002 | Wang et al. .................... 356/364 |
| 6,867,863 | B1 | | 3/2005 | Kadlec |
| 2005/0219528 | A1 | | 10/2005 | Wang |

FOREIGN PATENT DOCUMENTS

WO       2005001522       1/2005

* cited by examiner

*Primary Examiner* — Tri T Ton
(74) *Attorney, Agent, or Firm* — Hancock Hughey LLP

(57) ABSTRACT

Improving the throughput of systems for measuring birefringence of optical samples includes techniques for directing multiple beams through the photoelastic modulator component of the system so that, along with expanded detection mechanisms to accommodate the multiple beams, the heretofore scanning (via a single beam) of a line across the sample is considerably enlarged so that several lines covering a "swath" of the sample area is scanned by the system of the present invention.

20 Claims, 10 Drawing Sheets

Fig. 14a
Fig. 14b
Fig. 14c
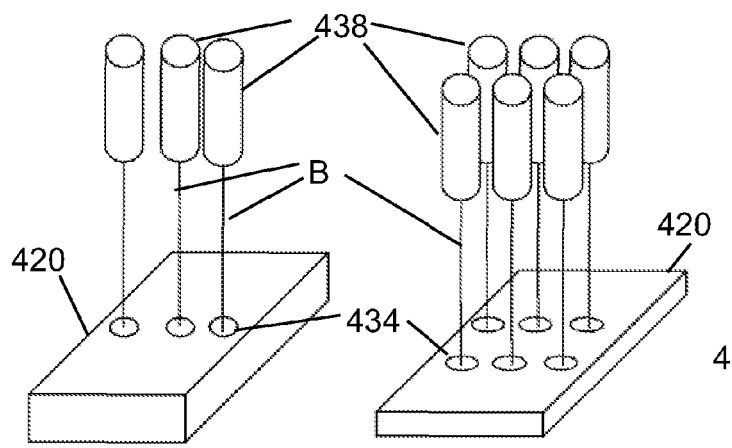
Fig. 14d
Fig. 14e
Fig. 14f
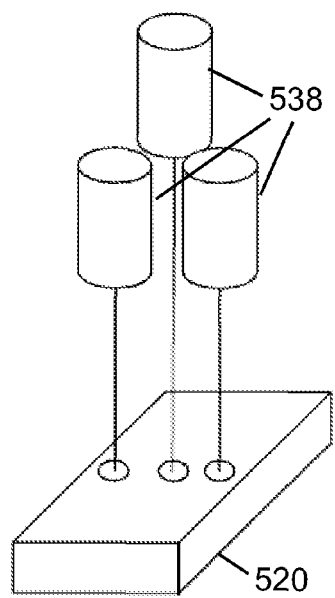
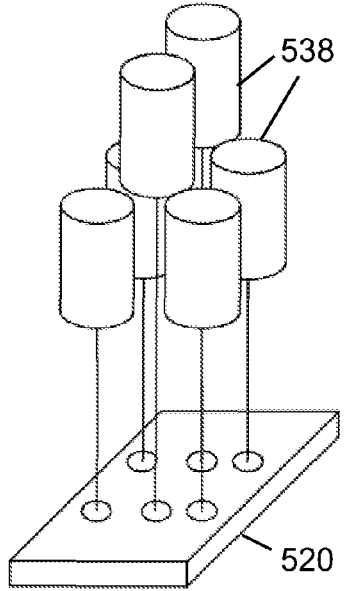
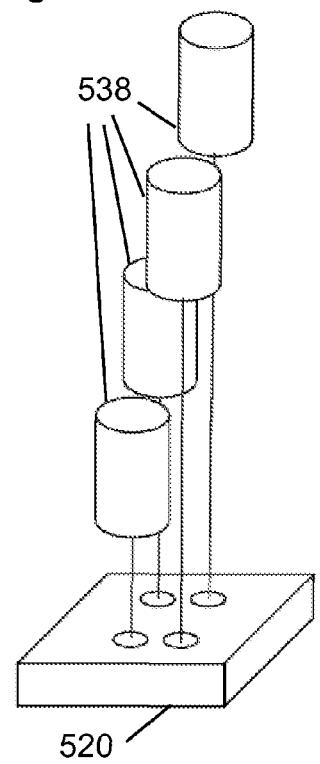

HIGH THROUGHPUT BIREFRINGENCE MEASUREMENT

This application is a National Stage of International Application No. PCT/US09/49614, filed Jul. 2, 2009, which claims the benefit of Provisional Application No. 61/079,120 filed Jul. 8, 2008.

TECHNICAL FIELD

This application relates to precise, high throughput measurement of birefringence in optical material such as polymeric films.

BACKGROUND

The term "birefringence" means that different linear polarizations of light travel at different speeds through light-transmissive optical material. Retardation or retardance represents the integrated effect of birefringence acting along the path of a light beam traversing the sample. If the incident light beam is linearly polarized, two orthogonal components of the polarized light will exit the sample with a phase difference, called the retardance. The fundamental unit of retardance is length, such as nanometers (nm). It is frequently convenient, however, to express retardance in units of phase angle (waves, radians, or degrees), which is proportional to the retardance (nm) divided by the wavelength of the light (nm).

Oftentimes, the term "birefringence" is interchangeably used with and carries the same meaning as the term "retardance." Thus, unless stated otherwise, those terms are also interchangeably used below.

U.S. Pat. Nos. 7,385,696 and 6,473,179, herein incorporated by reference, disclose systems for the precise measurement of birefringence in various optical materials. When so measured, the optical material is often referred to as a "sample." An important component of such systems includes a resonant polarization modulation device in the form of a photoelastic modulator or PEM.

In one approach, as illustrated and described in U.S. Pat. No. 6,473,179, the system for precisely measuring low-level birefringence properties of optical materials incorporates a single PEM for modulating a beam of polarized light that is then directed through a sample. The beam propagating from the sample is separated into two parts, with one part having a polarization direction different from the polarization direction of the other beam part. These separate beam parts are then processed as distinct channels. Detection mechanisms associated with each channel detect the time-varying light intensity corresponding to each of the two parts of the beam. The information is combined for calculating among other things, a precise measure of the retardance induced by the sample.

Another approach (as exemplified in an embodiments disclosed in U.S. Pat. No. 7,385,696) uses an optical setup that includes two PEMs to measure linear birefringence. This setup will be hereafter referred to as a dual PEM setup. This system of this embodiment can determine birefringence properties of optical materials such as polymeric films, as well as single-crystal materials such as quartz, calcite, mica, and sapphire. The birefringence of interest may be intrinsic to the material or induced by external forces.

The dual PEM setup generally comprises three modules. The top module includes a light source, a polarizer oriented at 45 degrees, and a PEM oriented at 0 degrees. The bottom module includes the second PEM that is set to a modulation frequency that is different from the modulation frequency of the first PEM. The second PEM is oriented at 45 degrees. The bottom module also includes an analyzer at 0 degrees and a detector. The middle module includes a sample support, which can be any of a variety of mechanisms for supporting a sample, such as polymeric film, etc., in position between the top and bottom modules to allow a light beam from the source of the setup to pass through the sample as described more below. The sample support may be of a type that mounts to a computer-controlled, movable X-Y stage to allow the sample to be scanned by the light beam across the area of the sample.

As a single beam is directed through a central optical aperture in the PEM, either the sample or the optical setup is moved so that the sample is scanned by the beam to enable multiple discrete measurements to be taken across the area of a sample to detect and graphically display variations in the birefringence properties across the sample area.

SUMMARY OF THE INVENTION

The present invention is directed to significantly improving the throughput of systems, such as those just described, for precisely measuring birefringence properties of optical materials. In this regard, techniques are provided for directing more than a single beam through a PEM so that, along with expanded detection mechanisms to accommodate the multiple beams, the heretofore scanning (via a single beam) of a line across the sample is considerably enlarged so that several lines covering a "swath" of the sample area is scanned by the system of the present invention. This approach greatly enhances the throughput of the system by minimizing the amount of time-consuming motion control required for moving components in a single-beam system across the entire area of the sample of interest.

In one embodiment, such as when particularly large-area samples are involved, the components for providing a multi-beam system of the present invention may themselves be multiplied or bundled to thereby increase the scanned swath of the combined components to any desired width, including the entire width of the sample so that the sample may be scanned in one pass.

The multiple beams through the PEMs (hence, through the sample) need not be limited to a single row extending across the sample (in a direction perpendicular to the direction of scanning) Rather, two or more rows of beams may be employed so that the sample can be advanced in steps or increments greater than a single step corresponding to a single row. For example, if three rows of beams are employed, the sample may be advanced from one location (as soon as retardance data is collected for that location) by a step distance or increment corresponding to the sum of those three rows. Assuming an insignificant time difference required for collecting data in three rows of beams as compared to one row, it will be appreciated that scanning using a system employing three beam rows will nearly triple the speed of scanning as compared to a single-row system.

Other advantages and features of the present invention will become clear upon study of the following portion of this specification and drawings.

BRIEF DESCRIPTION OF DRAWINGS

FIGS. 14*a*-14*j* are diagrams illustrating embodiments for providing sources for the multiple beams employed in systems utilizing the present invention.

DESCRIPTION OF PREFERRED EMBODIMENTS

While the US patents incorporated by reference here describe in detail the function carried out by the PEM components, an understanding of the present invention will be facilitated by a brief review of the general operation of a PEM in a birefringence measurement system.

Figure 1:
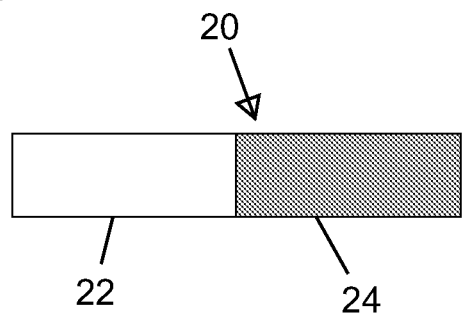
FIG. 1 is a diagram of a bar-shaped, single transducer PEM ("bar-type" PEM) that may be employed in a preferred embodiment of the present invention.

FIG. 1 depicts a diagram of a bar-shaped, single transducer PEM ("bar-type" PEM) 20. The optical element 22 can be, for example, fused silica, calcium fluoride, or other material. Bonded to one end of the optical element 22 is a crystal quartz piezoelectric transducer 24. In some embodiments, two transducers may be bonded to the optical element, one bonded to each end of the element. The optical element and transducer are sized so that when driven by the transducer, there is created in the PEM a standing ultrasound acoustic wave, at resonance. The bar-type PEM 20 is mounted to an enclosure and free to vibrate in the X-direction (left to right in FIG. 1).

The transducer is driven by a controller (not shown) to impart the oscillating birefringence to the optical element 22, preferably at a nominal frequency of 50 kHz. The PEM controller is adjustable to allow an operator to vary the drive frequency as well as the amplitude of the retardation introduced by the PEM.

Figure 2:
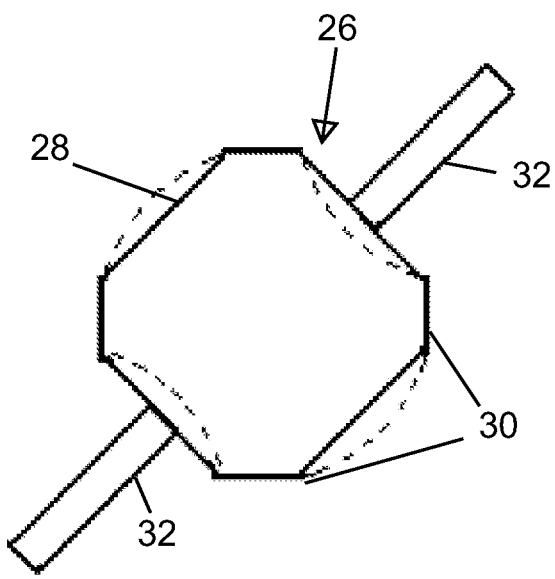
FIG. 2 is diagram of symmetrically shaped PEM ("symmetrical-type" PEM) having two transducers and that also may be employed in a preferred embodiment of the present invention.

FIG. 2 shows the symmetrical-type PEM 26, the optical element of which 28 employs a substantially square shape (top view) with beveled corners 30. Normally, the symmetrical-type PEM 26 is mounted to an enclosure via mounts extending between the enclosure and the beveled corners. Bonded to opposing sides of the optical element 26 are piezoelectric transducers 32.

The symmetrical-type PEM 26 generally offers a very good representation of both the physical shape and vibration mode of the optical element. Compared to the bar-type PEM 20, the symmetric PEM 26 provides a higher range of retardation modulation, a larger optical aperture and more symmetric retardation distribution across its area.

Returning to the discussion of a bar-type PEM 20 (FIG. 1), in a simplified model (extensional bar vibration mode), there is a one-dimensional standing acoustic wave established in the bar-shaped PEM. Thus the displacement, strain, and stress that are created during modulation are all distributed over the length of the optical element in the form of a sine function with different phases. The peak retardation distribution along the length of the optical element of the PEM will follow the form of a sine function (0 to $\pi$) with the maximum at the center of the optical element.

Figure 3:
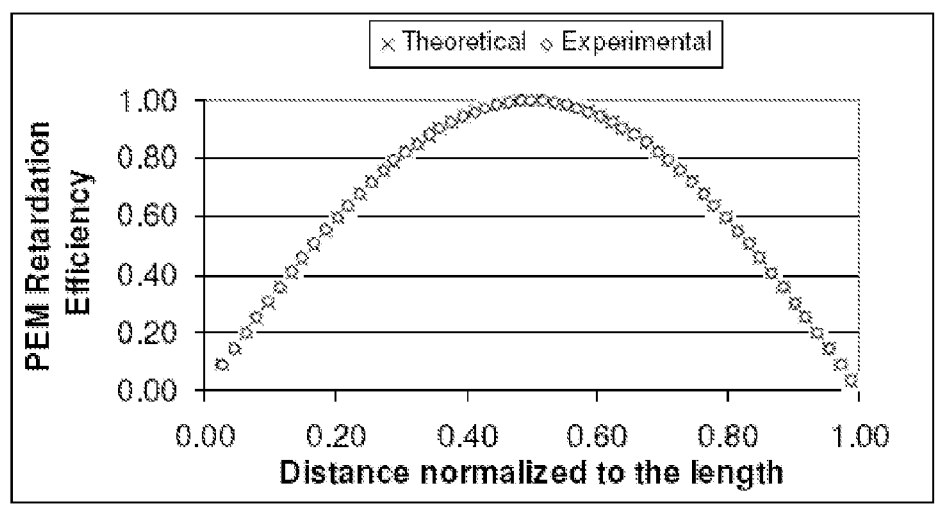
FIG. 3 is a diagram showing the peak retardation distribution, quantified as retardation efficiency scaled from 0.0 to 1.0, along the length of a bar-type PEM.

Considering, for example, a fused silica 50 KHz PEM, FIG. 3 illustrates that there are only minor differences between the experimental and theoretical data plotted in that figure, with a maximum difference of only 0.004. This very small difference between the experimental and theoretical data illustrates how closely the PEM operates to the simplified model of a resonating bar.

Figure 4:
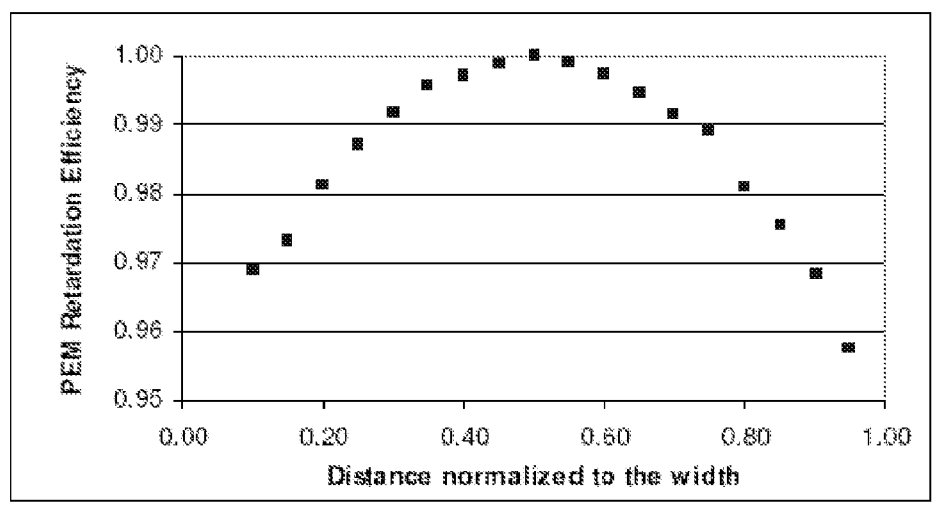
FIG. 4 is diagram showing the peak retardation distribution, quantified as retardation efficiency scaled from 0.0 to 1.0, along the width of a bar-type PEM.

Along the width of the optical element (Length>Width>Thickness), the PEM would ideally have unity retardation efficiency. However, the measured PEM retardation efficiency along the width of the optical element of the same PEM (of FIG. 3) is shown in FIG. 4. The retardation efficiency drops about 5% from the center to the edges of the optical element of the PEM.

Figure 5:
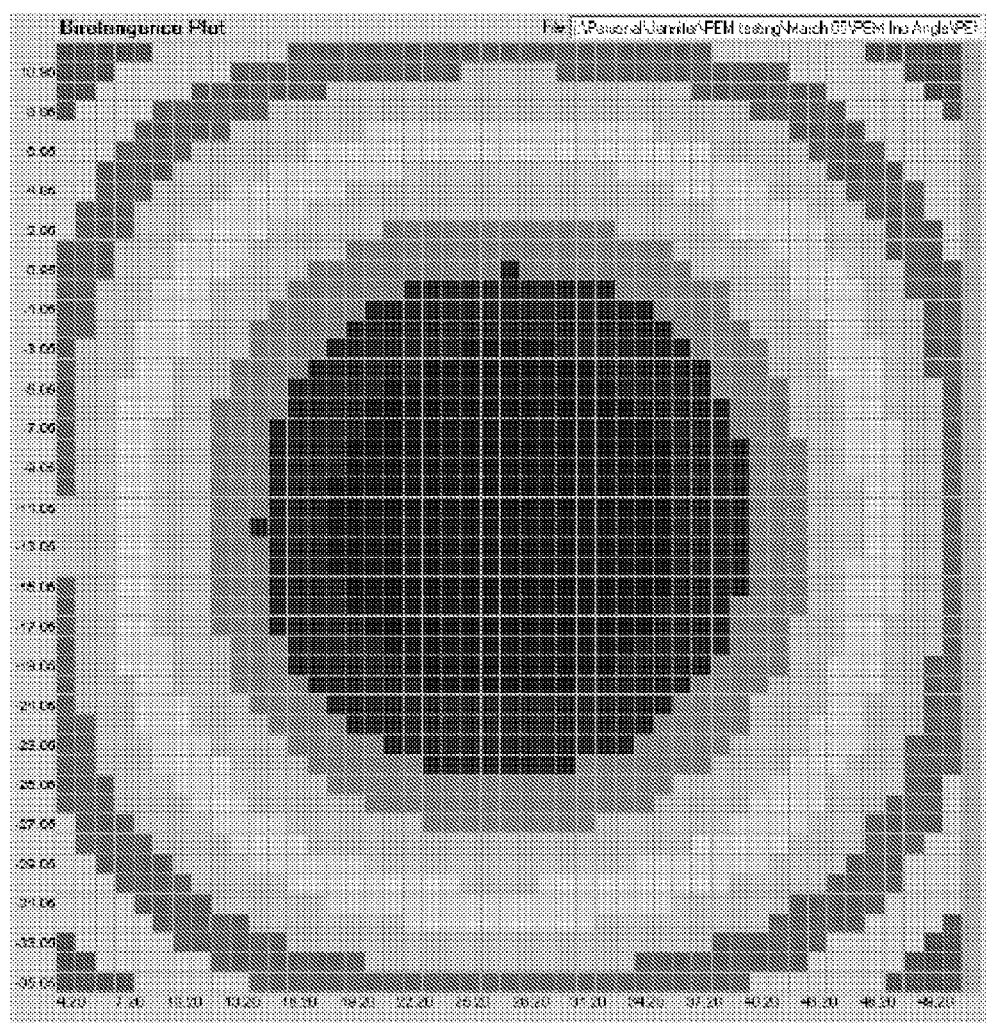
FIG. 5 is diagram showing the normalized retardation efficiency present in a symmetrical-type PEM.

The peak retardation for a typical symmetrical-type PEM (Hinds Instruments, PEM-90 model II/FS42 as diagrammed in FIG. 2; optical material: fused silica; frequency: 42 KHz) is plotted in FIG. 5. FIG. 5 displays retardation in the units of nanometers "nm" and the upper limit of the retardation is rounded up to an integer. The values of the normalized retardation efficiency are dimensionless and they have a range of 0 to 1. As seen, the peak retardation distribution is highly symmetrical with near circular symmetry in the central (darkest) portion of the optical element. Examining the middle row of the data plotted in FIG. 5 yields a good fit to the sine function.

In view of the foregoing, it will be appreciated that PEMs do not have uniform retardation modulation over their apertures. The value of the retardation modulation of a PEM is critical to accurately measuring polarization properties such as birefringence. Therefore, the present invention recognizes that the non-uniform retardation modulation over the aperture of a PEM must be addressed in applications where multiple light beams through the PEM are desirable for increasing the throughput of samples undergoing measurement of birefringence properties.

In accordance with the present invention, two or more beams of light are transmitted through the optical element of a PEM in a manner that addresses the issue of non-uniform retardation modulation over the aperture of a PEM. In this regard, the PEM's retardation distribution is first characterized across the optical aperture. This provides data enabling one to select a number of locations on the optical element that have substantially equal retardation points (that is, locations or points where the level of retardation modulation is known and substantially the same at all points, although not necessarily the maximum level that would occur, for example, in the center of the optical element). In the present embodiments of the invention, each of the multiple beams is directed through such a pre-characterized equal retardation point.

Figure 6:
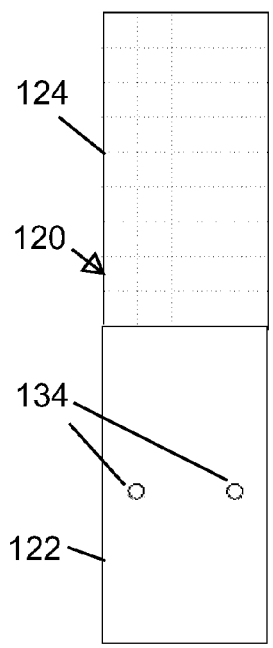
FIG. 6 is a top-view diagram of a bar-type PEM, with attached transducer, illustrating an embodiment where a single row of two light beams is transmitted through the optical element of the PEM.
Figure 7:
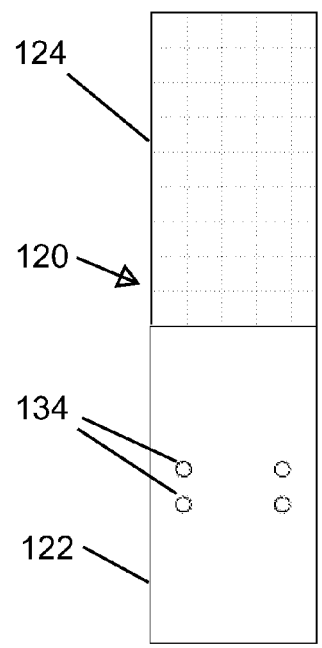
FIG. 7 is a top-view diagram of a bar-type PEM, with attached transducer, illustrating an embodiment where two rows of two light beams are transmitted through the optical element of the PEM.
Figure 8:
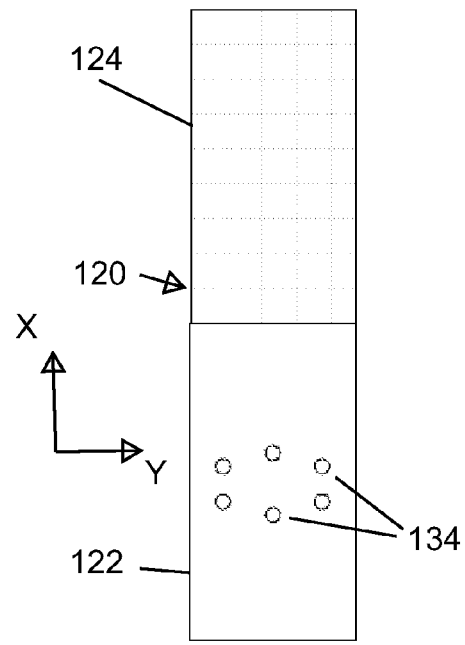
FIG. 8 is a top-view diagram of a bar-type PEM, with attached transducer, illustrating an embodiment where six light beams are transmitted through the optical element of the PEM.

FIGS. 6-8 show three examples of a bar-type PEM with multiple beams, each transmitted through an individual equal retardation point. In those figures, the top rectangular portion of the diagram represents the transducer 124, and the lower rectangle represents the optical element 122 of the PEM 120. Each of the small holes 134 represents a cross section of light beam propagating through the optical element (ie, though the plane of the figures).

FIG. 6 shows two beams spaced apart along a Y-axis (left to right in the figures) and located along that axis or width of the PEM transducer 122 at points having substantially equal retardation modulation.

FIG. 7 is like FIG. 6 but illustrates an example of two rows of two beams. The first row (Y direction) of beams, as well as the second row, is located along the width of the optical element so that the beams reside at equal retardation points. Similarly, each row is offset in the X direction (up and down in FIG. 7) from the center of the length of the PEM transducer 122 to ensure that uniformity of the retardation points in both the X and Y directions.

FIG. 8 depicts an example where eight beams are transmitted through the optical element and arranged relative to the X and Y directions so that the retardation modulation value at each point is essentially the same.

It is noteworthy here that the arrangement of multiple beams in two or more rows supplements the throughput increase provided by the use of multiple beams by also increasing the step size (in the X direction; vertical in FIGS. 6-8) undertaken during scanning of the sample, thereby increasing the speed of the scan. Such scanning movement can be accomplished by any of a variety of mechanisms, including conventional sample stages that are controllable for incrementally moving the sample in a translational sense along orthogonal (X and Y) axes.

Figure 9:
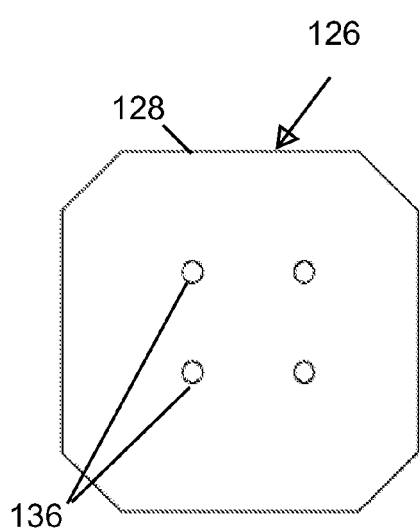
FIG. 9 is a top-view diagram of the optical element of a symmetrical-type PEM illustrating an embodiment where two rows of two light beams are transmitted through the optical element of the PEM.
Figure 10:
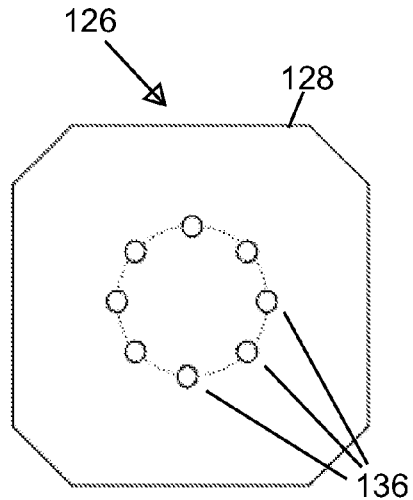
FIG. 10 is a top-view diagram of the optical element of a symmetrical-type PEM illustrating an embodiment where eight light beams are transmitted through the optical element of the PEM.

FIGS. 9 and 10 depict examples of multiple light beams transmitted through the optical elements 128 of symmetrical-type PEMs 126 (the transducers not shown in these figures) at equal retardation points. For example, FIG. 9 shows two rows of two beams 136 transmitted through the optical element 128. If one juxtaposes the distribution of those beams with the retardation distribution depicted in FIG. 5, it will be clear that the four points or locations of the beams fall along a single-shaded "circle" of FIG. 5, which circle represents a constant-value of retardation modulation for that PEM.

FIG. 10 illustrates how the four beams 136 in the FIG. 9 embodiment could be doubled to eight by placing the beams along a constant-retardation-value circle (shown in dashed lines) developed by characterizing the retardation efficiency of the symmetrical-type PEM.

Figure 11:
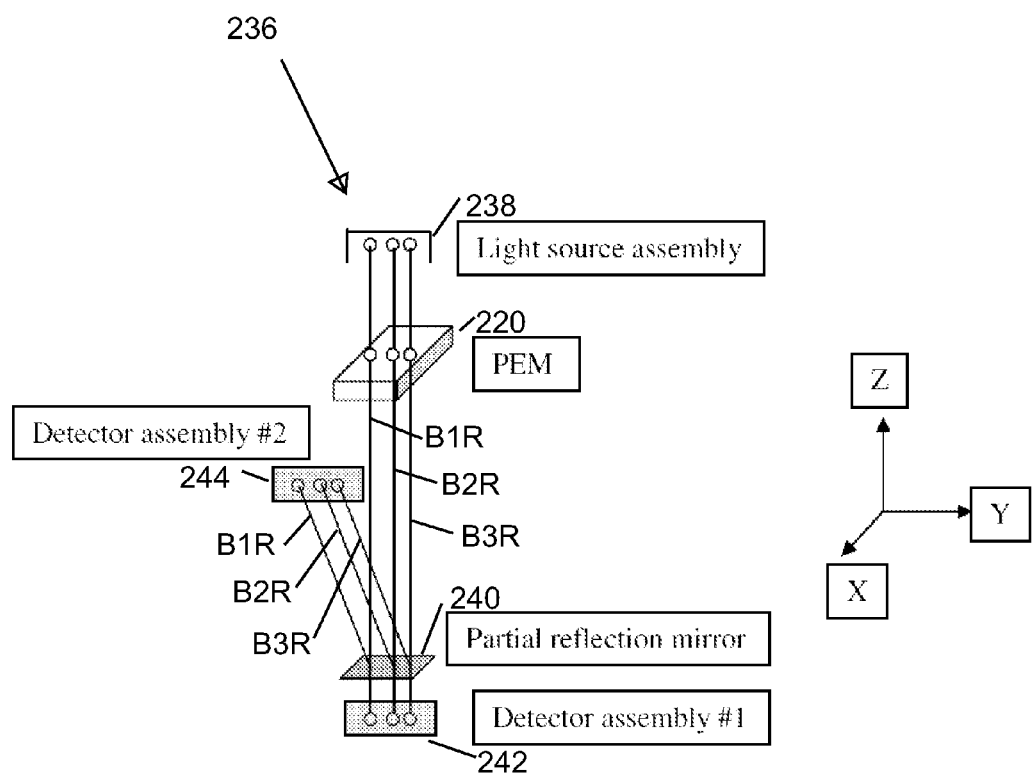
FIG. 11 is a diagram of one embodiment of a system that features an optical setup employing a single PEM through which three light beams are directed for increased throughput in measuring birefringence of a sample.

FIG. 11 is a diagram of one embodiment of a system 236 that features an optical setup employing a single PEM 220 through which three light beams from a source 238 are directed for increased throughput in measuring birefringence of a sample (not shown). It will be appreciated that, apart from the implementation of multiple beams, the setup shown there generally matches the embodiments depicted and described in the incorporated U.S. Pat. No. 6,473,179 (the '179 Patent).

The embodiment of FIG. 11 shows three light beams B1, B2, B3 passing through the PEM 220. Each beam is thereafter split and analyzed generally as described in the '179 patent. Specifically, the beams are passed through a partial reflection mirror 240 so that portions of the beams pass through the mirror to impinge upon a detector assembly 242 so that the intensity information of the beams is detected for further processing. Other portions of the beams are reflected by the mirror 240 as beams B1R, B2R, B3R at an angle that directs those reflected beams to a second detector assembly 244 so that the intensity information of the reflected beams is detected for further processing with the detected information of the other beams B1, B2, B3 to arrive at a birefringence value as explained in detail in the '179 Patent.

The scanning direction of the system 236 is the X direction in FIG. 11. Thus, one can readily appreciate that by tripling the number of beams as compared to the prior single-beam approach, the area scanned by the system in the X direction (that is, the width or swath of the sample across which the beams are scanned) is correspondingly tripled, thus greatly increasing the system throughput. In one embodiment, the spacing between beams may be as small as 20 mm or less.

Figure 12:
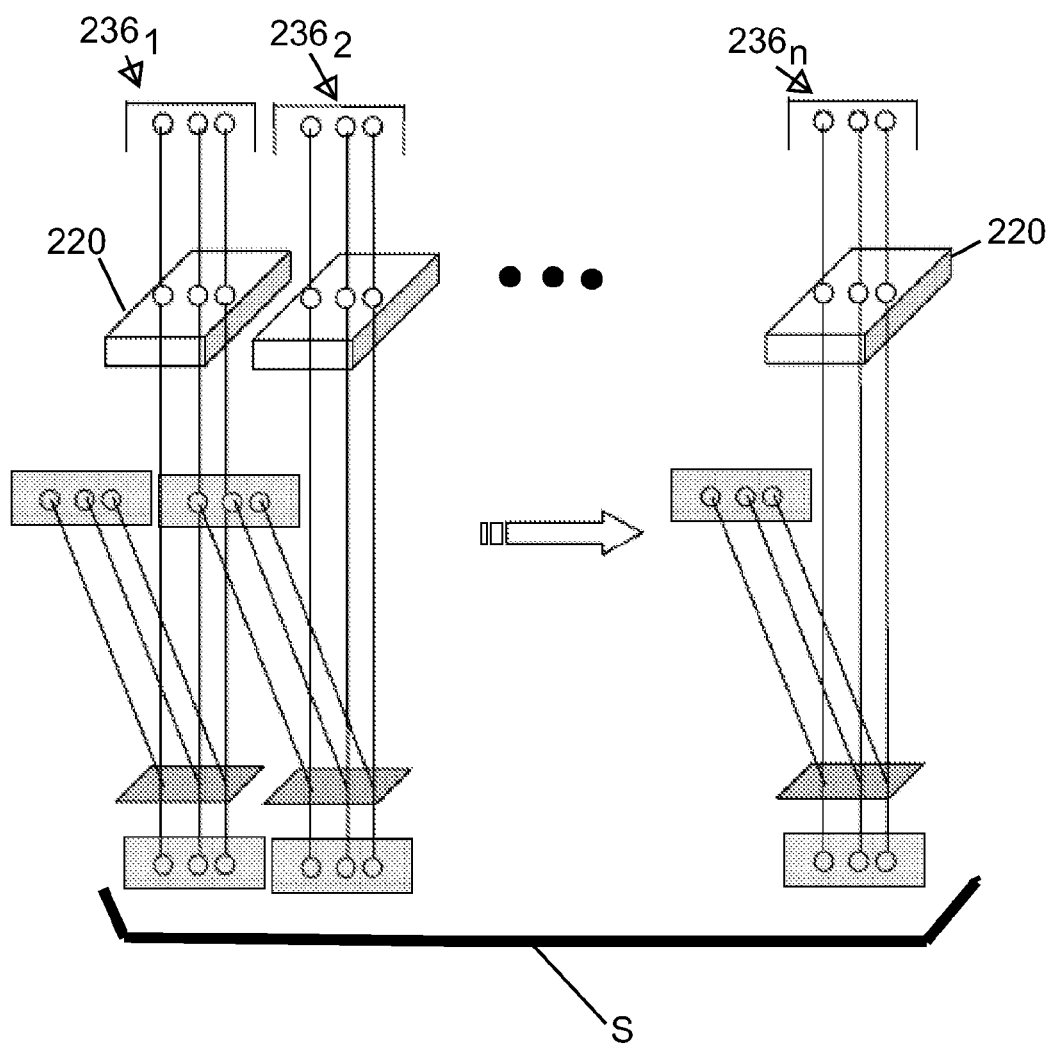
FIG. 12 is a diagram showing how systems such as that of FIG. 11 may be bundled to greatly increase the swath of the sample area that is scanned, hence increasing throughput.

FIG. 12 is a diagram showing how systems 236 as shown in FIG. 11 may be bundled (mounted immediately adjacent to one another) to greatly increase the swath "S" of the sample area that is scanned, hence increasing throughput. Any number of systems $236_1$, $236_2$ . . . $236_n$ may be bundled (the horizontal arrow in FIG. 12 pointing to the "nth" system) to thus multiply the benefits of the multi-beam swaths provided by each individual system.

Although FIGS. 11 and 12 appear to indicate that the three beams are aligned linearly across the width (Y direction, FIG. 11) of the PEMs 220, it will be understood that the central beam will in fact be offset therefrom in the X direction by an amount sufficient to place it at a point on the PEM optical element where the amount of retardation modulation matches that of the other two beams, as described more fully above.

Figure 13:
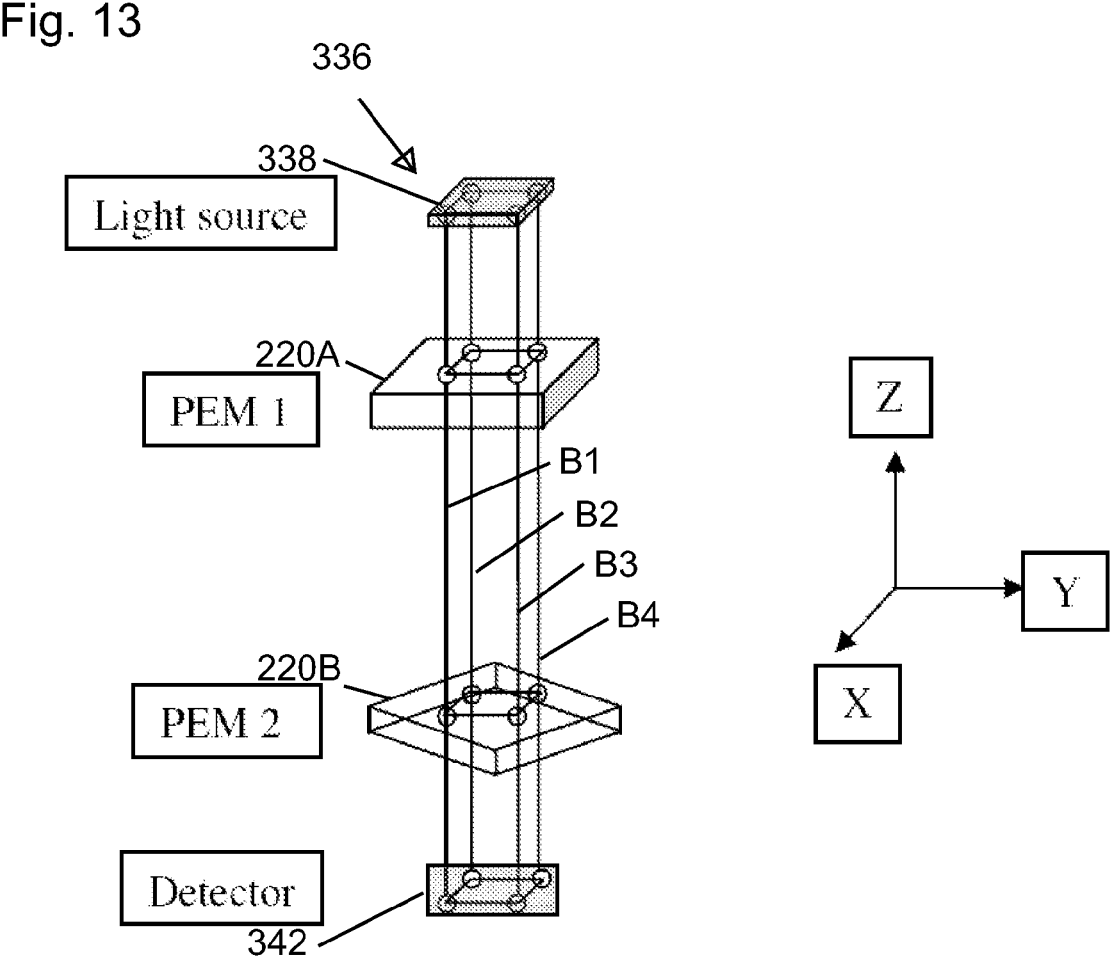
FIG. 13 is a diagram of another embodiment of a system that features a dual PEM optical setup and through which PEMs four beams are directed for increased throughput in measuring birefringence of a sample.

FIG. 13 is a diagram of another embodiment of a system 336 that features a dual PEM optical setup. This setup includes two PEMs 220A and 220B (with only the optical elements illustrated) and a light source assembly 338 for generating four spaced-apart beams B1, B2, B3, B4. The four beams are directed through the PEMs for increased throughput in measuring birefringence of a sample. It will be appreciated that, apart from the implementation of multiple beams, the setup shown there generally matches the embodiments depicted and described in the incorporated U.S. Pat. No. 7,385,696 (the '696 Patent). It is noteworthy here, however, that aperture size is a function of the PEM resonant frequency and in this embodiment (like those of the '696 Patent) the frequency of one PEM (PEM 1) 220A should not match that of the other PEM (PEM 2) 220B. Accordingly, in this embodiment the frequencies of the two PEMs 220A, 220B are selected to be very close, without matching, so that the aperture size through which the multiple beams pass are substantially the same, and so that there is no significant variation in the retardance distribution between the two PEMs. In this embodiment, the difference in the two PEM frequencies is held to about 3 KHz.

Moreover, like the systems depicted in FIGS. 11 and 12, the FIG. 13 system departs from that of the prior approach as respects the light source assembly 338 and detector assembly 342. Light source and detector assemblies suitable for the present invention are described next.

As shown in FIGS. 14a-14c, one way of providing a source of multiple beams B for transmission through the PEM 420 is to assemble an array of small LEDs, lasers, or other discrete light sources 438 (cylindrical elements in FIG. 14). In FIG. 14 the sources are shown transmitting the beams (vertical lines) through a PEM 420 with the holes 434 depicting the points on the PEM where the beams pass.

FIGS. 14d-14f illustrate how slightly larger light sources 538 may be arranged with some of the sources at different distances from the sample (that is offset in the Z direction) to ensure the proper resolution (minimum spacing between beams) of the beam locations on the PEM 520.

Figure 14G:
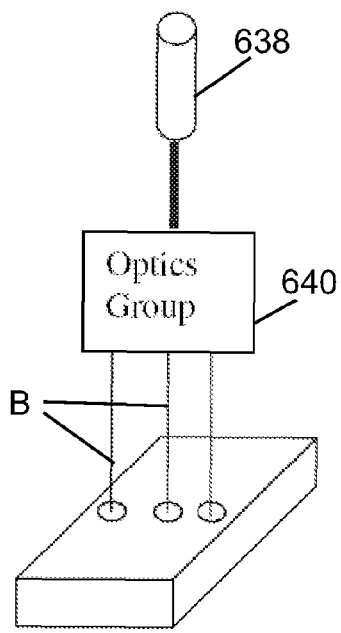
Figure 14H:
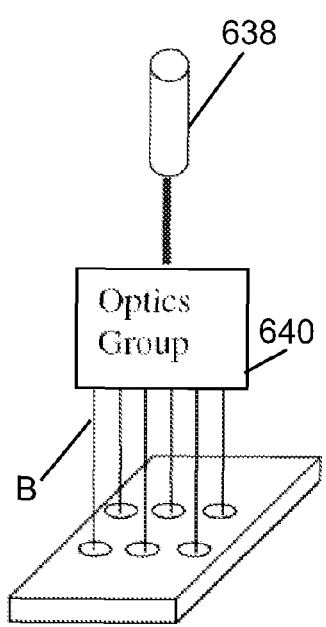
Figure 14I:
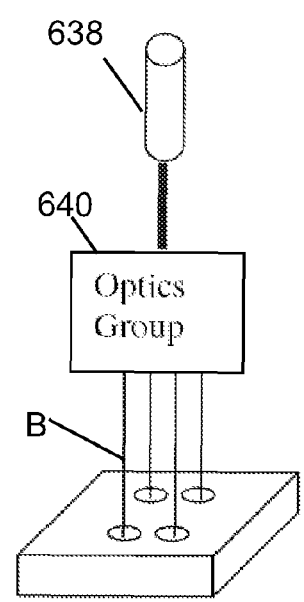

FIGS. 14g-14i illustrate how a single light source 638 may be split and collimated by conventional optical components (optics group 640) to provide the multiple beams B.

Figure 14J:
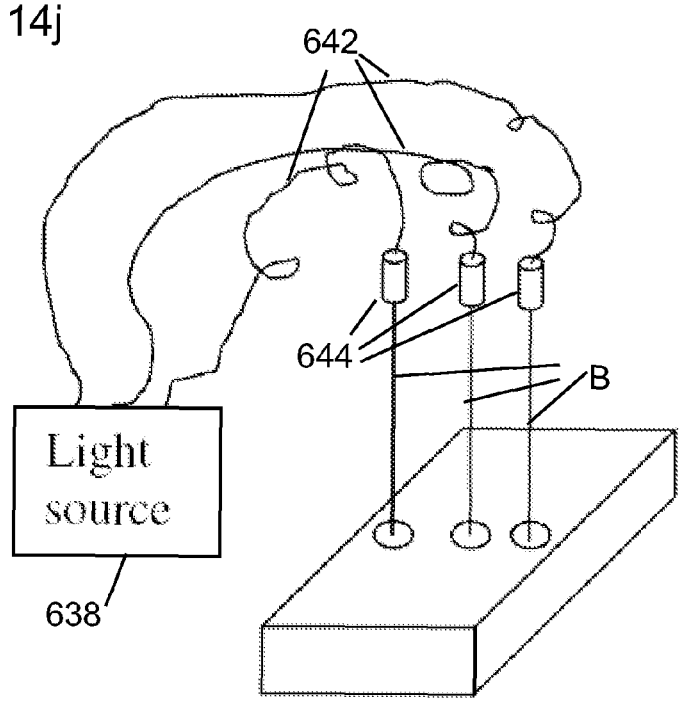

FIG. 14j illustrates how fiber optics 642 may be connected between a light source 638 and individual collimators 644 for providing the multiple beams B.

Figure 15:
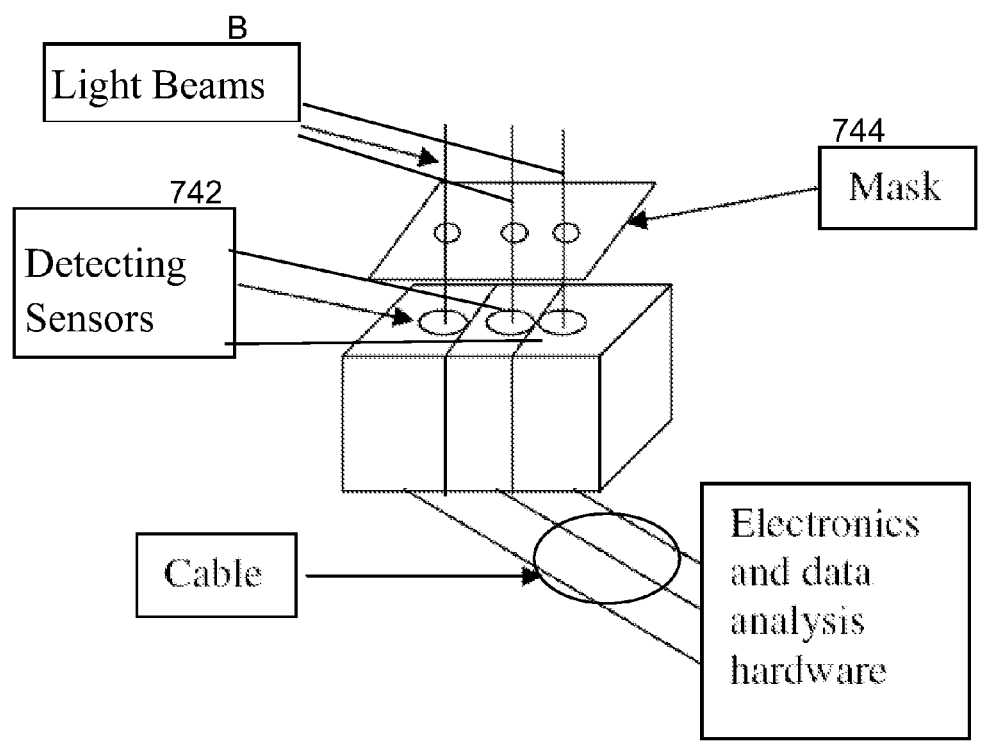
FIG. 15 is a diagram of a detector assembly for use in systems employing the multiple-beam approach of the present invention.

Modifications to the prior detection assemblies (ie, those depicted in the two US patents incorporated here by reference) are illustrated in FIG. 15. Specifically, each detector assembly includes multiple detecting sensors 742. The detecting sensors 742 have fairly large effective areas (several millimeters in diameter). When necessary, a mask 744 or masks with openings can be placed in front of the detectors for easy alignment and blocking unwanted light. In addition, large sheet polarizers are employed for use with such multiple source and detector setups.

The invention claimed is:

1. A method of arranging light beams that are used for measuring birefringence properties of a sample, comprising the steps of:
    generating from a source a plurality of spaced apart light beams;
    positioning between the source and the sample a polarization modulator that imparts levels of retardation in light beams that pass through an optical aperture that is associated with the polarization modulator;
    characterizing the retardation level distribution across the optical aperture to identify a plurality of locations where uniform levels of retardation are imparted by the polarization modulator; and
    arranging the plurality of light beams for passage through the locations so that the beams emanating from the polarization modulator to the sample will have substantially uniform retardation imparted therein.

2. The method of claim 1 wherein relative movement of the source and light beams is in an X direction during birefringence measurement, and the arranging step includes arranging the light beams in at least two rows wherein the rows are spaced apart in the X direction.

3. The method of claim 2 wherein one of the two rows comprises two light beams that are aligned in a Y direction that is perpendicular to the X direction and the other row includes a single light beam that is between in the Y direction the two beams of the one row.

4. The method of claim 1 wherein the generating step includes providing a plurality of discrete sources that emanate monochromatic light, one source for each light beam.

5. The method of claim 4 including the step of orienting the discrete sources at different distances from the sample thereby to minimize the spacing between the light beams that emanate from the sources.

6. The method of claim 1 wherein the generating step includes:
    providing a single-beam light source; and
    splitting and collimating the single beam emanating from the source.

7. The method of claim 1 wherein the generating step includes:
    providing a light source; and
    connecting a plurality of optical fibers to the source.

8. The method of claim 1 wherein the positioning step comprises positioning between the source and the sample a first photoelastic modulator driven to oscillate with a first modulation frequency.

9. The method of claim 8 including the steps of:
    providing a second photoelastic modulator so that the sample is between the first and second photoelastic modulators;
    setting the modulation frequency of the second photoelastic modulator to be different from the first modulation frequency; and
    minimizing the difference, thereby to minimize any difference between the distribution of retardation levels in the first and second photoelastic modulators.

10. The method of claim 9 wherein the modulation frequency of the first and second photoelastic modulators is set to be about 3 KHz.

11. The method of claim 1 wherein the characterizing step comprises identifying locations having the same, uniform levels of retardation imparted by the polarization modulator, and wherein the arranging step results in none of the plurality of light beams passing through locations other than the identified locations.

12. An optical setup for high throughput birefringence measurement, comprising
    a light source assembly;
    an optical sample for which birefringence measurement is sought;
    a polarization modulator positioned between the light source assembly and the optical sample and oscillated for imparting retardation in light beams that pass through the modulator, the level of the imparted retardation being variable and dependent upon the location where in the modulator the light beams pass through;
    wherein the light source assembly is configured to direct a plurality of monochromatic light beams through predetermined locations in the modulator such that the level of retardation imparted in the beams is uniform for all beams.

13. The optical setup of claim 12 including means for imparting incremental relative movement between the sample and the light beams in a scanning direction and wherein the light source assembly is configured to direct the beams in two or more rows that are spaced apart in the scanning direction.

14. The optical setup of claim 12 wherein the light source assembly comprises a plurality of discrete light sources.

15. The optical setup of claim 14 wherein the discrete light sources are arranged to be at various distances from the polarization modulator, thereby to enable minimizing the distance between the light beams that emanate from each light source.

16. The optical setup of claim 12 wherein the polarization modulator is a first photoelastic modulator driven by a transducer.

17. The optical setup of claim 16 including a second photoelastic modulator located so that the sample is between the first and second photoelastic modulators, the first and second photoelastic modulators having pre-characterized locations where a uniform level of retardation is imparted in the light beams passing therethrough.

18. A system for one-pass scanning of an optical sample of a given width with monochromatic light beams, comprising a first optical setup as defined in claim 12 and one or more additional optical setups as defined in claim 12, the optical setups arranged to enable one-pass scanning of an optical sample of a given width with monochromatic light beams.

19. A method for one-pass scanning of an optical sample of a given width and length with monochromatic light beams for determining the birefringence characteristics of the sample across the area of the sample, comprising the steps of:

directing a row of light beams through at least one photo-elastic modulator at locations in the modulator where retardation imparted in each beam by the modulator will be substantially uniform among all of the beams; and then directing the row of light beams through the sample and across the width of the sample; and incrementally moving the sample relative to the beams across the length of the sample; and detecting the intensity of the beams for determining the birefringence characteristics of the sample across the area of the sample.

20. The method of claim 19 wherein the directing step directs a plurality of rows of light beams through the photoelastic modulator, the rows being spaced apart in a direction along the length of the sample, and wherein the incrementally moving step includes moving the sample relative to the beams in increments corresponding to the spacing of the plurality of the rows.

* * * * *